US00PP32925P2

(12) United States Plant Patent
Kordes

(10) Patent No.: US PP32,925 P2
(45) Date of Patent: Mar. 30, 2021

(54) MINIATURE ROSE PLANT NAMED 'KORPOT089'

(50) Latin Name: *Rosa hybrida*
Varietal Denomination: KORpot089

(71) Applicant: W. KORDES' SÖHNE Rosenschulen GmbH & Co KG, Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/602,926

(22) Filed: Dec. 30, 2019

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122, 129
CPC ..... A01H 5/0222
See application file for complete search history.

(56) References Cited

U.S. PATENT DOCUMENTS

PP18,840 P2 5/2008 Kordes
PP25,004 P2 10/2014 Kordes

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of miniature rose plant, herein referred to by its cultivar name, 'KORpot089', is provided which forms abundantly on a substantially continuous basis attractive, medium-red colored blossoms. Attractive vigorous vegetative is formed, which contrasts beautifully with the blossoms. The growth habit is compact. The new variety is well suited for providing attractive ornamentation in the landscape.

1 Drawing Sheet

Botanical/commercial classification:
Latin name: *Rosa hybrida.*
Varietal denomination: 'KORpot089'.

The new variety of *Rosa hybrida* Miniature Rose Plant of the present invention was created during 2014 at Offenseth-Sparrieshoop, Germany by artificial pollination wherein two parents were crossed which previously had been studied in the hope that they would contribute the desired characteristics. The female parent (i.e., seed parent) of the new variety was the 'KORsinski' variety (non-patented). The male parent (i.e., pollen parent) of the new variety was the 'KORpolare' variety (U.S. Plant Pat. No. 18,840).

The parentage can be summarized as follows:

'KORsinski' x 'KORpolare'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, medium-red colored blossoms,
(b) displays a compact growth habit, and
(c) exhibits vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORsinski' variety (i.e., the seed parent) displays larger flowers compared to the new variety. In addition, the 'KORpolare' variety (i.e., the pollen parent) displays higher petal count than the new variety and exhibits a bushy to upright growth habit, whereas the new variety displays a compact and bushy growth habit. Moreover, the new variety can be readily distinguished from other similar non-parental varieties. For example, the 'KORpot028' variety (U.S. Plant Pat. No. 25,004) displays flowers with less petals compared to the new variety and exhibits an upright to bushy habit, whereas the new variety exhibits a compact and bushy growth habit.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot089'.

The first offer for sale was Jan. 1, 2019 by the inventor or another who obtained the new variety directly or indirectly from the inventor.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Odense, Denmark while growing indoors on its own roots in 10.5 cm containers.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during September, while growing in a one-gallon container on its own roots in a greenhouse in Cochranville, Pa.

Commercial classification: Miniature Rose Plant.

Plant:

*Habit*.—Compact and bushy.

*Height*.—Approximately 35.0 cm on average.

*Width*.—Approximately 35.0 cm on average.

Branches:

*Stem color*.—Commonly near Yellow-Green Group 144A.

*Length*.—Main stems: approximately 20.0 cm on average. — secondary stems: approximately 17.0 cm on average.

*Diameter*.—Main stems: approximately 5.0 mm on average. — secondary stems: approximately 3.0 mm on average.

*Texture*.—Glabrous.

*Thorns*.—Young thorns: sparse amount; color is commonly near Greyed-Orange Group 177B; length is approximately 6.0 mm on average; and width is approximately 5.0 mm on average at point of attachment. — old thorns: number is typically 1-2 per internode; length is approximately 4.0 mm on average; width is approximately 5.0 mm at attachment; color is commonly near Greyed-Orange Group 177B.

Foliage:

*Young foliage color*.—Upper surface: commonly near Green Group 137C with indistinguishable venation. — under surface: commonly near Green Group 138B with indistinguishable venation.

*Old foliage color*.—Upper surface: commonly near Green Group 139A with venation of near Green Group 139B. — under surface: commonly near Green Group 139B with venation of near Green Group 139C.

*Petiole*.—Upper and under surfaces: texture is smooth; color is commonly near Yellow-Green Group 144A. — length: approximately 2.5 cm on average. — diameter: approximately 1.0 mm on average.

*Rachis*.—Color: upper surface is commonly near Yellow-Green Group 144A, under surface is commonly near Green Group 143C. — length: approximately 5.0 cm on average. — diameter: approximately 1.0 mm on average. — texture: upper surface is smooth, lower surface is smooth with a few small prickles.

*Stipules*.—Length: approximately 1.5 cm on average. — width: approximately 4.0 mm on average. — margin: entire to erose. — color: upper surface is commonly near Yellow-Green Group 144A, under surface is commonly near Yellow-Green Group 144B.

*5-leaflet leaf*.—Length: approximately 9.5 cm on average. — width: approximately 7.0 cm on average.

*Leaf arrangement*.—Alternate.

Leaflets:

*Number of leaflets*.—3, 5, and 7.

*Shape*.—Ovate; apex is acute; and base is rounded.

*Leaflet margin*.—Serrate.

*Glossiness of upper side of leaflet*.—Semi-glossy.

*Venation*.—Pattern: reticulate. — color: upper surface is commonly near Greyed-Red Group 178A for the main vein and indistinguishable from the leaf color for all other veins; lower surface is indistinguishable from the leaf color.

*Texture*.—Upper and under surfaces is smooth.

*Terminal leaflet*.—length: approximately 4.5 cm on average. — width: approximately 3.4 cm on average.

*Lower leaflet*.—Length: approximately 3.0 cm on average. — width: approximately 2.6 cm on average.

Inflorescence:

*Number of flowers*.—Generally about 3-5 blooms on average on a plant at once.

*Number of blooms per stem*.—Typically 1-2 blooms per stem on average.

*Peduncle*.—Length: approximately 4.0 cm on average. — diameter: approximately 8.0 mm on average. — surface texture: glabrous. — strength: strong. — color: commonly near Yellow-Green Group 144A.

*Sepals*.—Number: commonly 5. — length: approximately 2.7 cm on average. — width: approximately 8.0 mm on average. — margin: entire with occasional extensions on two or three sepals measuring approximately 3.0 mm in length on average and 3.0 mm in width on average. — upper surface color and texture: commonly near Yellow-Green Group 144A; covered in short pubescence. — under surface color and texture: commonly near Yellow-Green Group 144A; puberulent. — shape: lanceolate. — apex: acute to aristate. — base: truncate or flat as it joins the receptacle.

*Bud*.—Shape: globular to pointed. — length: approximately 2.0 cm on average. — width: approximately 1.5 cm on average. — color: commonly near Red Group 53B.

*Flower*.—Diameter: approximately 6.5 cm on average. — height: approximately 3.5 cm on average. — duration: flower is on the plant approximately 21 days. — form: double, cuplike. — profile: convex. — number of petals under normal conditions: approximately 43 petals on average. — shape of the petal: — overall: broadly obovate. — apex: round. — base: cuneate. — petal length: inner petals are approximately 2.5 cm on average; outer petals are approximately 3.0 cm on average. — petal width: inner petals are approximately 2.0 cm on average; outer petals are approximately 3.5 cm on average. — petal margin: entire. — petal drop: good. — fragrance: light sweet scent. — petal color when first and fully open: — upper and under surfaces: commonly near Red Group N45A with a very small basal spot of near White Group 155D. — petal texture: upper and lower surfaces are glabrous. — petaloids: typically 8 per flower; color of upper and under surfaces is commonly near Red Group N45A with a very small basal blotch of near Yellow Group 10C; length is approximately 2.5 cm on average; width is approximately 1.9 cm on average; texture is smooth; margin is variable, entire to erose; shape is variable, oblong and mostly curving inward; apex is round; base is cuneate.

*Receptacle*.—Color: commonly near Yellow-Green Group 144A. — diameter: approximately 8.0 mm on average. — surface texture: smooth. — shape: round.

*Stamen*.—Number is approximately 85 on average. — anthers: number is approximately 85 on average; color is commonly near Yellow-Orange Group 21C; length is approximately 2.5 mm on average; and shape is oval. — filaments: length is approximately 3.0 mm on average and color is commonly near Yellow Group 11A.

*Pistils*.—Arrangement is separate and free; number is approximately 95 on average. — styles: length is less than 6.0 mm on average and color is mostly near Red-Purple Group 58B and some exhibiting a small hint of near Yellow Group 11C at the base of the stigma. — stigmas: diameter is typically less than 1.0 mm; color is commonly near Yellow Group 12A; shape is fan shaped.

*Ovary*.—Color is commonly near White Group 155D; length is approximately 2.0 mm on average, and width is approximately 1.0 mm on average.

*Pollen*.—None observed.

*Hips*.—None observed.

Development:

*Vegetation*.—Dark green, vigorous and strong.

*Blooming*.—Abundant and reblooms well from a trim.

*Hardiness*.—Unknown.

*Resistance to disease*.—Good resistance to *Botrytis* (*Botrytis cinerea*) and powdery mildew (*Sphaerotheca pannosa*) diseases under normal greenhouse growing conditions in Cochranville, Pa.

*Pest resistance/susceptibility*.—None observed to date.

Plants of the 'KORpot089' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) forms attractive, medium-red colored blossoms, (b) displays a compact growth habit, and (c) exhibits vigorous vegetation;

substantially as herein shown and described.

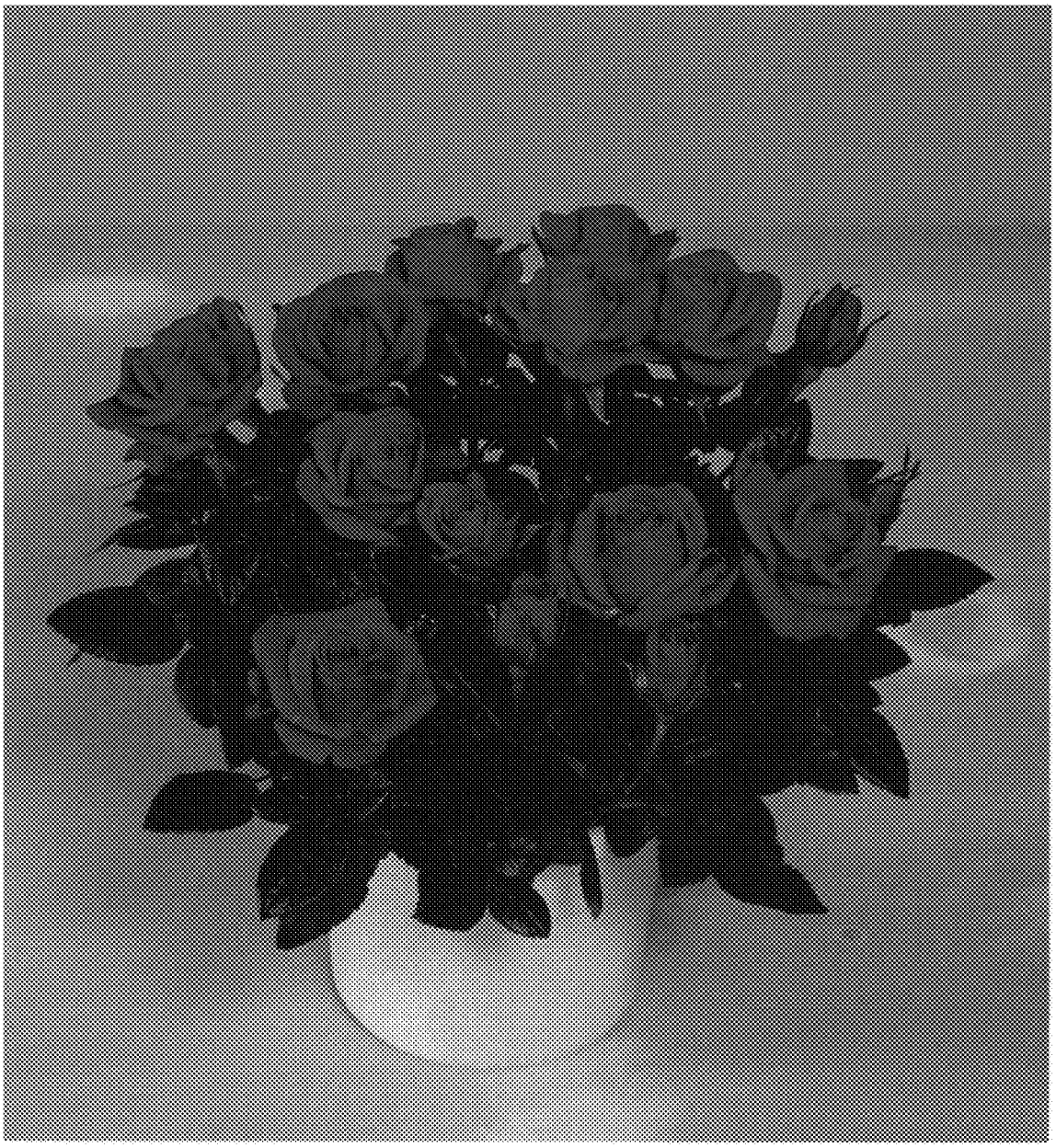

* * * * *